(12) United States Patent
Paxton et al.

(10) Patent No.: US 9,095,296 B2
(45) Date of Patent: Aug. 4, 2015

(54) THERAPEUTIC GUM IRRIGATOR

(75) Inventors: Christine M. Paxton, Sterling, IL (US); Keith Dirks, Sterling, IL (US)

(73) Assignee: C. Paxton Designs, Inc., Sterling, IL (US)

( * ) Notice: Subject to any disclaimer, the term of this patent is extended or adjusted under 35 U.S.C. 154(b) by 533 days.

(21) Appl. No.: 13/489,116

(22) Filed: Jun. 5, 2012

(65) Prior Publication Data
US 2013/0122453 A1 May 16, 2013

Related U.S. Application Data

(60) Provisional application No. 61/628,957, filed on Nov. 10, 2011.

(51) Int. Cl.
| | |
|---|---|
| *A61C 17/02* | (2006.01) |
| *A61B 1/24* | (2006.01) |
| *A61C 17/028* | (2006.01) |
| *A61H 13/00* | (2006.01) |
| *A61C 17/00* | (2006.01) |
| *A61B 1/015* | (2006.01) |
| *A61C 1/08* | (2006.01) |

(52) U.S. Cl.
CPC . *A61B 1/24* (2013.01); *A61B 1/015* (2013.01); *A61C 1/088* (2013.01); *A61C 17/00* (2013.01); *A61C 17/02* (2013.01); *A61C 17/0202* (2013.01); *A61C 17/028* (2013.01); *A61H 13/005* (2013.01)

(58) Field of Classification Search
CPC ............ A61C 17/0211; A61C 17/036; A61C 17/0205; A61C 17/02; A61C 17/225; A61C 17/227; A61C 1/0088; A61C 17/0202; A61H 13/00; A61H 13/005; A61H 2201/12; A61H 2201/1253; A61B 1/24; A61B 1/015
USPC ......... 601/162, 160, 161, 163, 165, 154, 139; 433/80, 89
See application file for complete search history.

(56) References Cited

U.S. PATENT DOCUMENTS

| | | | | |
|---|---|---|---|---|
| 3,144,867 | A * | 8/1964 | Trupp et al. | 433/88 |
| 3,452,745 | A * | 7/1969 | Spitz et al. | 601/162 |
| 3,858,767 | A * | 1/1975 | Borin | 222/494 |
| 4,236,889 | A * | 12/1980 | Wright | 433/86 |
| 4,375,964 | A * | 3/1983 | Knopp et al. | 433/29 |
| 4,619,612 | A * | 10/1986 | Weber et al. | 433/80 |
| 4,634,376 | A * | 1/1987 | Mossle et al. | 433/29 |

(Continued)

*Primary Examiner* — Justine Yu
*Assistant Examiner* — Tu Vo
(74) *Attorney, Agent, or Firm* — Greer Burns & Crain Ltd.

(57) ABSTRACT

A therapeutic gum irrigator is provided for subgingival periodontal irrigation with a chemotherapeutic fluid. The irrigator includes a housing surrounding at least a portion of the irrigator, a reservoir connected to the housing to retain the fluid, and a cannula configured for subgingival periodontic insertion in fluid communication with the reservoir. The irrigator further includes a neck connected to the housing and separating the reservoir from the cannula. A pump in fluid communication with the reservoir and the cannula includes a displacing element movable between first and second positions and a biasing element that biases the displacing element to the first position. A lever connected to the housing can mechanically move the displacing element to the second position, expelling a predefined volume of the fluid through the cannula. The biasing element causes the displacing element to return to the first position upon release of the thumb lever by the user.

11 Claims, 5 Drawing Sheets

(56) References Cited

U.S. PATENT DOCUMENTS

| | | | |
|---|---|---|---|
| 4,648,838 A * | 3/1987 | Schlachter | 433/29 |
| 4,779,173 A * | 10/1988 | Carr et al. | 362/109 |
| 4,902,225 A * | 2/1990 | Lohn | 433/80 |
| 5,033,961 A * | 7/1991 | Kandler et al. | 433/89 |
| 5,683,246 A * | 11/1997 | Coss et al. | 433/29 |
| 5,741,132 A * | 4/1998 | Usui et al. | 433/30 |
| 5,897,314 A * | 4/1999 | Hack et al. | 433/29 |
| 5,908,295 A * | 6/1999 | Kawata | 433/29 |
| 6,095,810 A * | 8/2000 | Bianchetti | 433/29 |
| 6,202,242 B1 * | 3/2001 | Salmon et al. | 15/22.1 |
| 6,561,802 B2 * | 5/2003 | Alexander | 433/29 |
| 7,163,397 B2 * | 1/2007 | Hahn et al. | 433/89 |
| 7,677,888 B1 * | 3/2010 | Halm | 433/29 |
| 8,328,553 B2 * | 12/2012 | Broyles et al. | 433/90 |
| 2004/0209222 A1 * | 10/2004 | Snyder et al. | 433/80 |
| 2005/0004498 A1 * | 1/2005 | Klupt | 601/162 |
| 2007/0203439 A1 * | 8/2007 | Boyd et al. | 601/162 |
| 2008/0008979 A1 * | 1/2008 | Thomas et al. | 433/80 |
| 2009/0202961 A1 * | 8/2009 | Fani et al. | 433/119 |
| 2010/0151414 A1 * | 6/2010 | Paxton et al. | 433/90 |
| 2011/0144588 A1 * | 6/2011 | Taylor et al. | 604/151 |
| 2012/0045730 A1 * | 2/2012 | Sayder et al. | 433/29 |

* cited by examiner

THERAPEUTIC GUM IRRIGATOR

This application claims priority under 35 U.S.C. §119 from provisional application Ser. No. 61/628,957, filed Nov. 10, 2011.

FIELD OF THE INVENTION

This invention relates to periodontal irrigators, and more particularly to therapeutic gum irrigators for patients' home use.

BACKGROUND OF THE INVENTION

Recent epidemiology suggests a link between periodontal health and systemic health, and several trials support this association. Research links periodontal disease to other health issues including heart disease, stroke, diabetes, pre-term low term birth weight, rheumatoid arthritis, and chronic kidney disease. Moreover, periodontal disease often results in chronic inflammatory response to bacterial infection in the periodontal pockets.

An estimated 80% of adults in America have some form of periodontal disease that, if left untreated, could lead to tooth loss. Periodontal disease, including gingivitis and periodontitis, is a chronic bacterial infection that affects the gums and bone surrounding and supporting the teeth.

In an initial form of periodontal disease (gingivitis), the gums redden, swell and bleed easily. If left untreated, gingivitis can lead to periodontis, which is caused by plaque bacteria spreading and growing below the gum line. This bacteria irritates the gums, which in turn stimulates a chronic inflammatory response in which the gums separate from the teeth, deepening periodontal pockets (spaces between the teeth and gums that frequently become infected), and allowing the infection to advance.

Professional scaling and root planing are necessary to remove the attached bacteria from the surface of the roots. However, additional home care between professional treatments is helpful to maintain periodontal health. Traditional oral cleansing tools such as toothbrushes and dental floss are useful for maintaining periodontal health of already-healthy gums. However, these traditional tools are limited in that they generally can clean pockets only up to approximately 2-3 mm in depth. Gum inflammation, loss of epithelial attachment between the gums and teeth, and/or deterioration of the alveolar process caused by periodontitis results in deepening of the periodontal pockets, so that brushing and flossing are no longer sufficient to fully cleanse the pockets.

Subgingival irrigation with an antimicrobial agent helps to disrupt bacterial colonization between professional treatments, even in relatively deep periodontal pockets. Moreover, irrigation is a useful procedure in controlling inflammation and keeping tissue healthy between professional periodontal therapies. Thus, supragingival and subgingival irrigation is effective at helping control gingivitis and periodontitis. However, the overwhelming challenge for treatment is to encourage patient compliance with regular professional and home care.

Generally, research has been devoted to variable pulsing irrigation that delivers a great volume of fluid in a relatively non-directed manner that is analogous to rinsing. While such a system may be capable of delivering relatively large quantities of high-pressure fluid, it is economically impractical to employ such a system with a relatively high-cost chemotherapeutic cleansing fluid. Thus, there is a need for a delivery system that accurately delivers a precisely measured quantity of chemotherapeutic fluid in a directed manner for patient use.

SUMMARY OF THE INVENTION

In one aspect of the present invention, a therapeutic gum irrigator is provided for subgingival periodontal irrigation with a chemotherapeutic fluid. The irrigator includes a housing surrounding at least a portion of the irrigator, a reservoir connected to the housing to retain the fluid, and a cannula configured for subgingival periodontic insertion in fluid communication with the reservoir. The therapeutic gum irrigator further includes a neck connected to the housing and separating the reservoir from the cannula. A pump is in fluid communication with both the reservoir and the cannula, and includes a displacing element movable between first and second positions, and a biasing element that biases the displacing element to the first position. A lever connected to the housing can mechanically move the displacing element to the second position, expelling a predefined volume of the fluid through the cannula. The biasing element causes the displacing element to return to the first position upon release of the thumb lever by the user.

DETAILED DESCRIPTION

A therapeutic gum irrigator for home use is described below. The irrigator allows a user to perform periodontal irrigation between visits to a treating professional. The irrigator allows for subgingival irrigation with a fluid, including a chemotherapeutic/bactericidal fluid, a fluoride-containing fluid, and/or water. Depending on the type of fluid used, the process of irrigation helps to cleanse periodontal pockets through mechanical disruption of a plaque biofilm within the cavity and/or bactericidal effect of the irrigating fluid. Moreover, the fluid may contain an anti-inflammatory and/or analgesic component to help relieve symptoms of periodontitis. The fluoride fluid component may help to desensitize root surfaces and to arrest or prevent root caries. The therapeutic gum irrigator is designed to facilitate ergonomic irrigation of a user's periodontal pockets, but may also be used by a lay person or treating professional to irrigate periodontal pockets of a patient. In this context, treating professionals include, but are not limited to, oral hygienists, dentists, periodontists, and/or oral surgeons.

Figure 1:
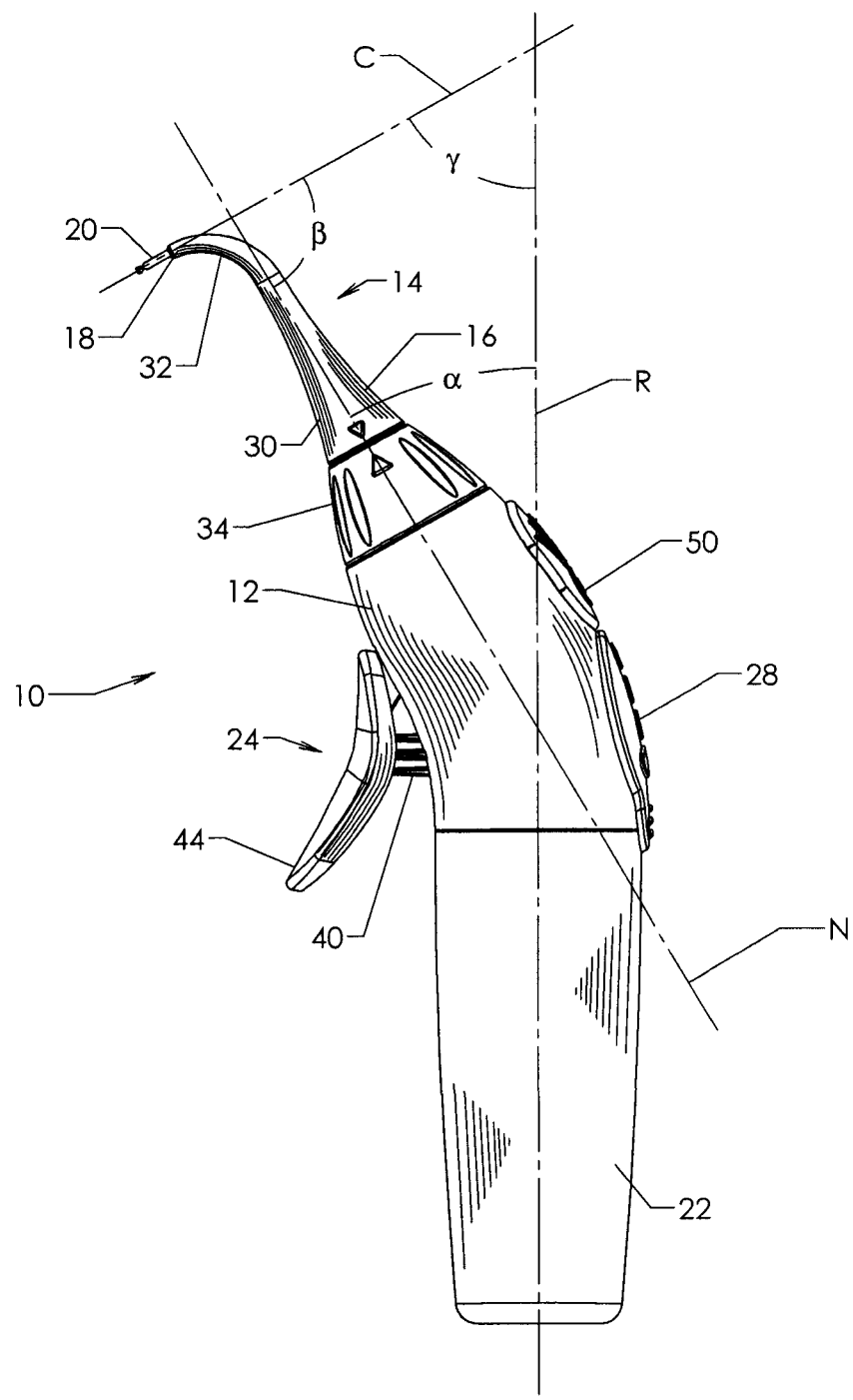
FIG. 1 is a side plan view of an embodiment of the therapeutic gum irrigator of the present invention.
Figure 2:
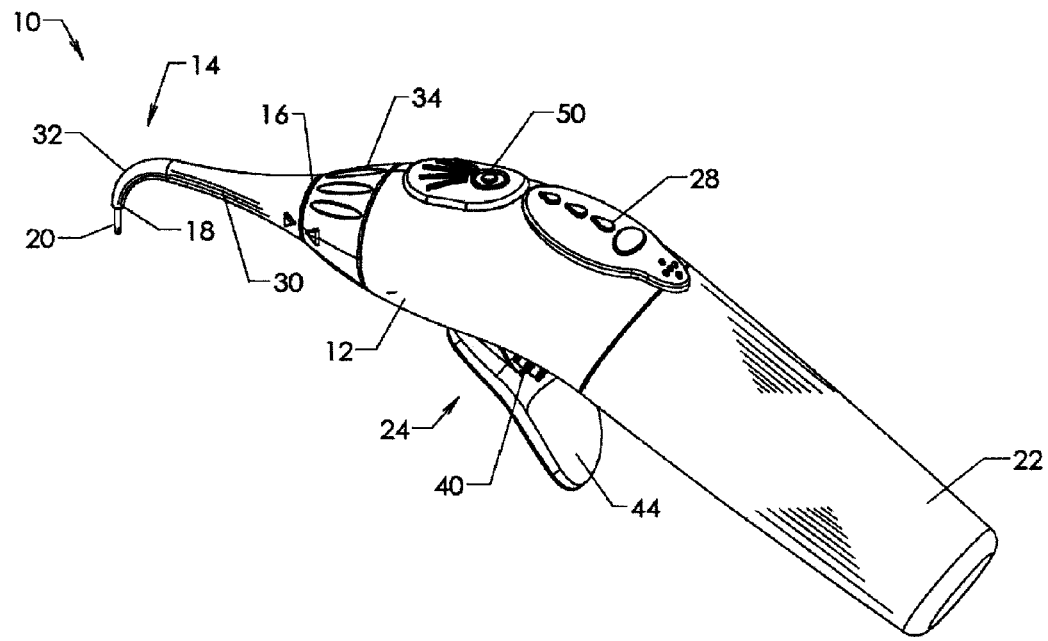
FIG. 2 is a side perspective view of the therapeutic gum irrigator of FIG. 1.

As seen in FIGS. 1 and 2, a therapeutic gum irrigator 10 has a housing 12 connected to a neck 14. The neck 14 includes a proximal end 16 that connects the neck to the housing 12, and a distal end 18. A cannula 20 for subgingival application of a fluid to a user's periodontal pockets depends from the neck distal end 18.

The housing 12 is shaped such that a user can easily and comfortably manipulate the therapeutic gum irrigator 10. Further, the housing is removably connected to and preferably at least partially surrounds a generally cylindrical reservoir 22 and a pump 24. The housing 12 defines a fill opening 26 (FIG. 3) that allows a user to fill the reservoir 22 without need to remove the reservoir. A cover 28 is hingedly attached to the housing 12 and covers the fill opening 26. When closed, the cover 28 and housing 12 preferably form a substantially water-tight barrier to help prevent liquid from escaping the reservoir 22. The cover 28 is preferably attached to the housing 12 via a biased hinge, such as a biased living hinge or a spring-biased barrel hinge, such that the cover 28 is biased towards a closed position. However, artisans will recognize that additional biased and non-biased hinge options are within the scope of the invention.

The reservoir 22 is preferably formed from a relatively light weight, resilient material, such as plastic or acrylic, and is preferably transparent or translucent so a user can easily monitor the fluid in the reservoir. As shown in FIG. 1, the reservoir 22 generally defines a reservoir axis R, which passes through the center of the reservoir.

The neck 14 is generally J-shaped, having a straight portion 30 adjacent to the proximal end 16, and an arcuate portion 32 adjacent to the distal end 18. Preferably, the neck 14 is formed from a relatively soft, resilient biocompatible acrylic, plastic, or rubber material, but those of skill in the art will recognize that any known biocompatible material may be used to form the neck. The neck 14 serves to connect the cannula 20 to the housing 12. As shown in FIG. 1, the straight portion 30 defines a neck axis N passing through a center of the straight portion. The neck axis N is angled obliquely relative to the reservoir axis R. This helps to ergonomically position the cannula 20 for proper subgingival insertion.

Preferably, the neck 14 is connected to the housing 12 by a rotatable coupler 34. The coupler 34 is generally coaxial with the straight portion 30 of the neck 14, and allows the neck to rotate about the neck axis N. This rotation may be a smooth rotation about the axis N to allow for arbitrary positioning of the neck, or there may be one or more predefined positions at which the rotation is halted, for example by detents in the rotational coupling or other known systems. The rotational coupler 34 allows for positioning of the neck 14 and cannula 20 to help allow easy, ergonomic access to all four quadrants of the user's mouth without need to rotate the housing 12.

The cannula 20 is a hollow tube formed from a resilient biocompatible material, such as metal, plastic, or acrylic. The cannula 20 is preferably generally cylindrical, though one of skill in the art will recognize that other shapes are possible without departing from the scope of the invention. The cannula 20 depends from the arcuate portion 32 of the neck 14, and defines a cannula axis C passing through the center of the cannula. The cannula axis C is oriented such that the axis C is not parallel with the reservoir axis R or the neck axis N. Preferably, the axes C and N are approximately orthogonal, though all orientations of the axis C that are non-parallel with axes N and R are contemplated. Accordingly, an angle $\alpha$ is formed between the reservoir axis R and neck axis N. Similarly, an angle $\beta$ is formed between the neck axis N and the cannula axis C, and an angle $\gamma$ is formed between the cannula axis C and the reservoir axis R. Preferably, $\beta$ is approximately equal to 90°, and $\alpha$ is approximately equal to 90–$\gamma$. The angles $\alpha$, $\beta$, and $\gamma$ are selected to help ensure that relatively difficult to reach portions of the mouth, such as distal areas of the back molars, are accessible. Accordingly, those of skill in the art will recognize that other angles may be selected without departing from the scope of the invention.

The cannula 20 is sized for subgingival insertion, and to accurately direct fluid to an area selected by the user, such as a periodontal pocket. In some embodiments, the cannula may direct the fluid in a single direction. Other embodiments include side ports on the cannula, allowing for a more dispersed flow of the fluid.

Figure 3:
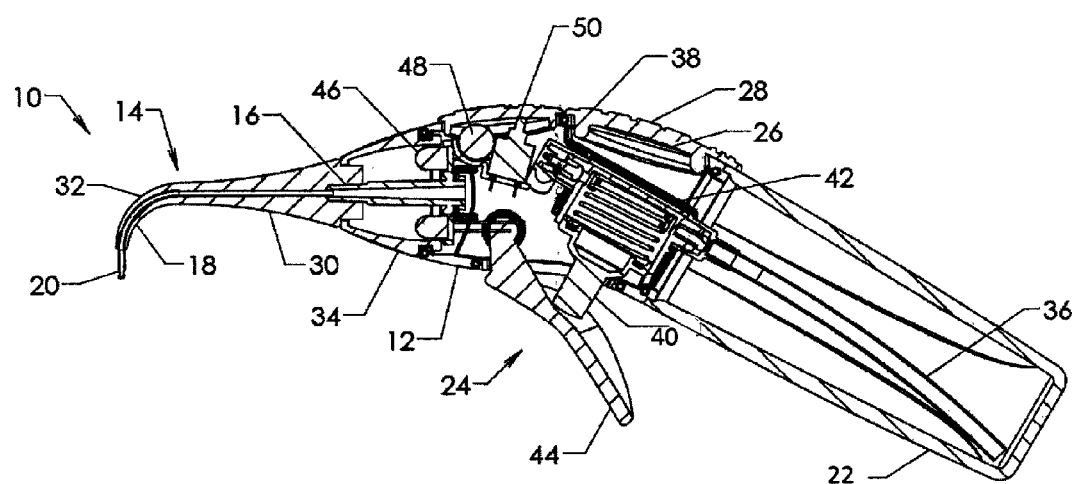
FIG. 3 is a cross-sectional view of the therapeutic gum irrigator of FIG. 1.

Turning now to FIG. 3, a cross-sectional view of the therapeutic gum irrigator 10 is shown. The pump 24 is preferably a single-acting, single-cylinder positive displacement reciprocating pump as shown in FIG. 2; however, artisans will recognize that other pumps may be used without departing from the scope of the invention. The pump 24 is disposed such that an intake siphon 36 extends into the reservoir 22. A pump outlet 38 is in fluid communication with the cannula 20. The intake siphon 36 includes a one-way valve allowing fluid to flow from the reservoir 22 to the pump 24, but preventing fluid flow in the opposite direction. Similarly, the outlet 38 includes a one-way valve allowing fluid to flow from the pump 24 to the cannula 20, but preventing opposite-direction flow.

The pump 24 further includes a displacing element such as piston 40 movable between first and second positions, and a biasing element such as biasing spring 42 biasing the piston to the first position. A mechanical actuator lever 44 is hingedly connected to the housing 12 and positioned to mechanically move the piston 40 to the second position.

In operation, a user applies force to the lever 44 sufficient to overcome the biasing force of the biasing spring 42. This user-applied force causes piston 40 to move from the first position to the second position. As the piston 40 moves, it displaces fluid in the pump, causing the fluid to be flow through the pump outlet 38 to be expelled at the cannula 20. Once the user releases the lever 44, the biasing spring 42 causes the piston 40 to return to the first position, inducing fluid flow from the reservoir 22 into the pump 24 via intake siphon 36.

Those of skill in the art will recognize that the volume of fluid displaced by each actuation of the pump 24 is proportional to both the cross-sectional area of the piston and the piston travel distance. Preferably, area and travel distance are selected so that the volume of displaced fluid is within a range of about 1-4 ml. However, larger and smaller volumes are contemplated. Additionally, a pressure at which fluid is expelled from the cannula 20 is a function of the selected fluid volume and a cross-sectional area of the cannula. Thus, it is preferable that the fluid volume and cannula cross-sectional area are chosen so that the pressure produced is sufficient to irrigate the pockets without causing damage to the surrounding tissue or causing undue discomfort to the user/patient.

The therapeutic gum irrigator 10 can include a light source 46 positioned to illuminate at least an area surrounding the cannula 20. The light source 46 may include one or more light emitting diodes, fluorescent bulbs and/or incandescent bulbs. Electrically coupled to the light source 46 is a power source 48 such as a battery, and an operating switch 50. The operating switch 50 is disposed in a position to open or close a circuit including the light source and battery, thereby enabling or disabling flow of electricity from the power source 44 to the light source 46. The switch 50 is preferably a known electrical switch such as a biased normally-open switch or a toggle switch, but those of skill in the art will recognize that other switches may be used without departing from the scope of the invention. The light source 46 is arranged near the rotatable coupler 34. Preferably, at least portions of the neck 14 and cannula 20 are formed from a transparent or translucent material to allow for better illumination.

Figure 4:
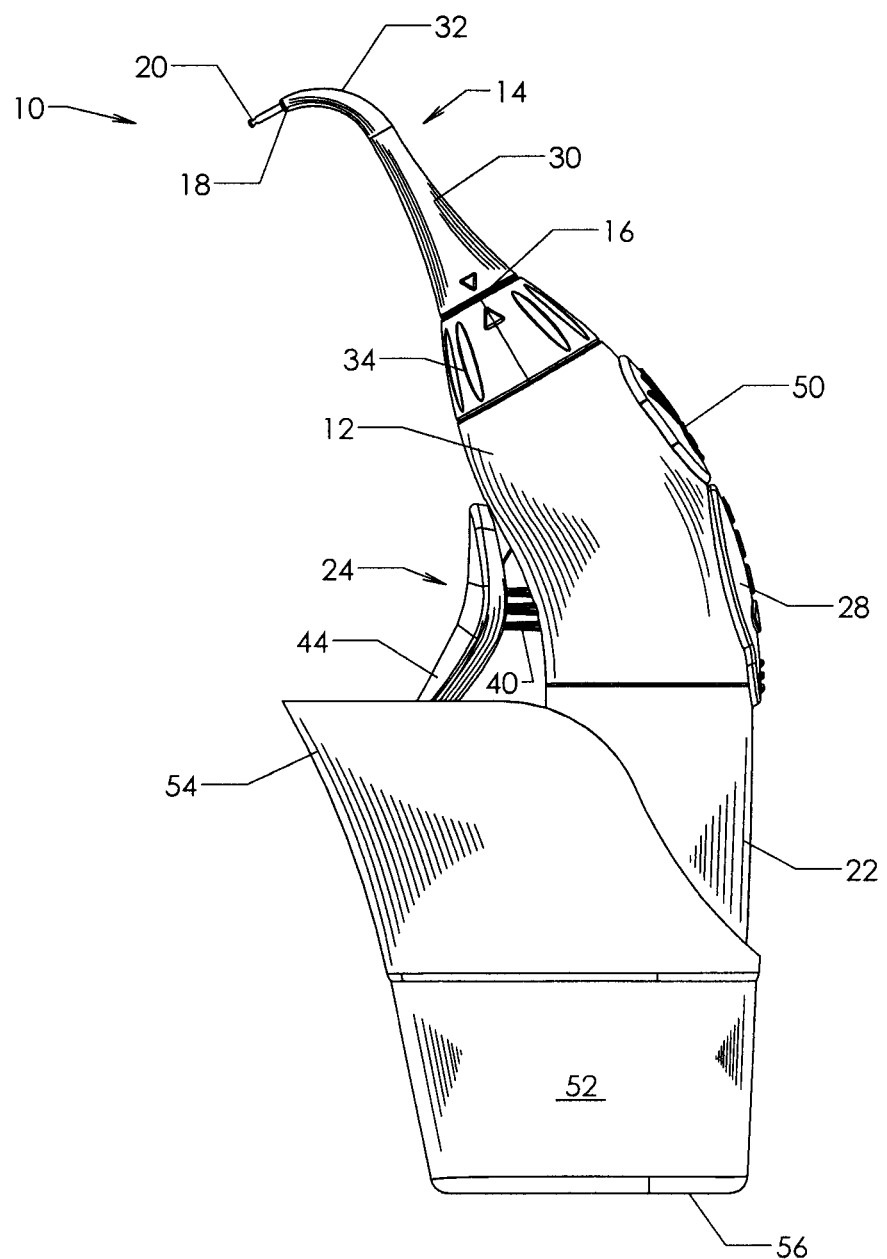
FIG. 4 is a side plan view the therapeutic gum irrigator of FIG. 1 disposed within a filling cup.
Figure 5A:
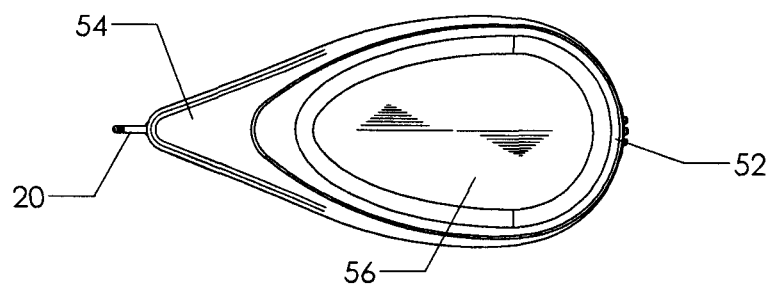
FIG. 5A is a bottom plan view of the irrigator and filling cup of FIG. 4.
Figure 5B:
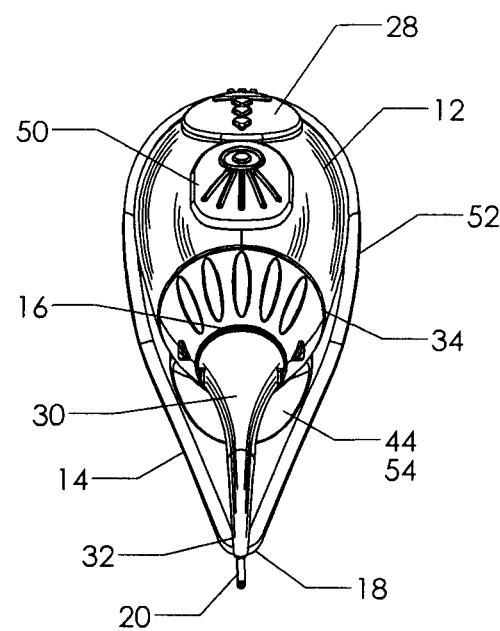
FIG. 5B is an overhead plan view of the irrigator and filling cup of FIG. 5A.

Turning now to FIGS. 4, 5A, and 5B, the therapeutic gum irrigator 10 preferably further includes a filling cup 52 to aid a user in filling the therapeutic gum irrigator 10. The cup 52 is sized such that a volume of the cup is substantially similar to a volume of the reservoir 22. Preferably, the cup 52 may include gradations indicating volume, and is preferably formed from a transparent or translucent material to easily allow a user to determine a volume of fluid contained in the cup. The cup 52 further includes a pour spout 54 having a size and shape selected to aid a user in transferring fluid from the cup to the reservoir 22 via the fill opening 26 formed in the housing 12. Alternatively, the reservoir 22 may be detached from the housing 12 and filled directly, with or without use of the fill cup 52. As shown in FIGS. 5A and 5B, the cup 52 can have a tear-drop shape, with a relatively wide portion and a tapered spout 54. This allows the cup to rest comfortably in a user's hand, while adequately directing liquid.

A base 56 of the fill cup 52 is sized to accommodate a base of the reservoir 22 when the fill cup is not being used to fill the reservoir. Optionally, the base 56 may be sized to closely fit at least a portion of the reservoir 22, such that the therapeutic gum irrigator 10 is removably engaged with the cup 52 by a frictional fit.

Figure 6:
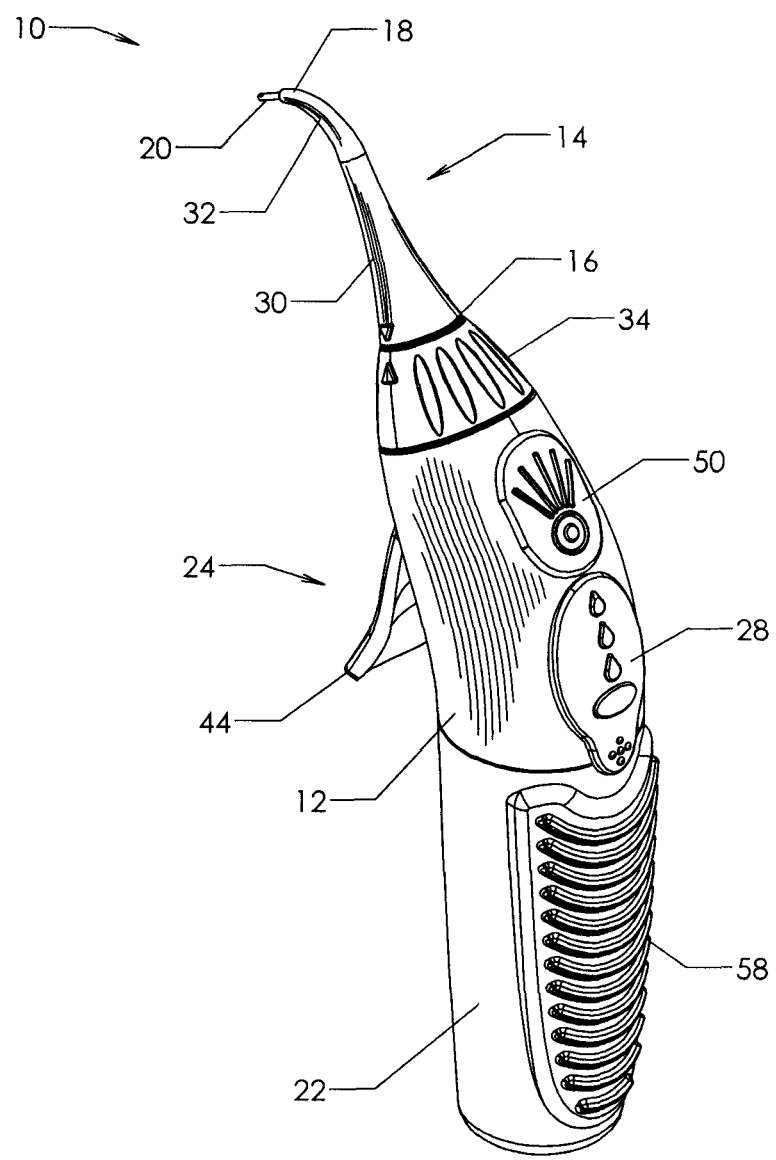
FIG. 6 is a rear perspective view of an alternate embodiment of the therapeutic gum irrigator of the present invention.

Turning to FIG. 6, the housing 12 surrounding at least a portion of the therapeutic gum irrigator 10 may include a textured coating 58 to aid the user in gripping the irrigator. The coating 58 is preferably formed from a soft-touch plastic or rubber, though any material suitable for forming the housing 12 could also be used to form the coating.

While the principles of the invention have been described above in connection with specific apparatus and applications, it is to be understood that this description is made only by way of example and not as a limitation on the scope of the invention.

What is claimed is:

1. A therapeutic gum irrigator for subgingival periodontal irrigation with a chemotherapeutic fluid, comprising:
   a housing surrounding at least a portion of the therapeutic gum irrigator;
   a reservoir connected to said housing and configured to retain the chemotherapeutic fluid;
   a cannula in fluid communication with said reservoir, said cannula configured for subgingival insertion;
   a translucent or transparent neck operatively connected to said housing, said cannula being inside of said translucent or transparent neck;
   a pump in fluid communication with both said reservoir and said cannula,
   a light source secured to said housing near the location where the translucent or transparent neck is operatively connected to said housing, the light source illuminating an area near said cannula by passing light through said translucent or transparent neck;
   the light source having at least two lights;
   an electrical source sufficient to power said light source;
   a mechanical switch configured to selectively allow flow of electricity from said electrical source to said light source; and wherein said translucent or transparent neck is operatively connected to said housing by a rotatable coupler, said light source being inside said rotatable coupler.

2. The therapeutic gum irrigator of claim 1, wherein said translucent or transparent neck includes a substantially straight portion and an arcuate portion.

3. The therapeutic gum irrigator of claim 2, wherein said straight portion of said translucent or transparent neck defines an axis that is oblique relative to an axis defined by said reservoir.

4. The therapeutic gum irrigator of claim 3, wherein said cannula defines an axis that is oblique to said axis defined by said straight portion of said translucent neck or transparent neck, and to said axis defined by said reservoir.

5. The therapeutic gum irrigator of claim 4, wherein said axis defined by said cannula is substantially orthogonal to said axis defined by said straight portion of said translucent neck.

6. The therapeutic gum irrigator of claim 1, wherein said housing defines an opening and is configured to allow fluid to enter said reservoir.

7. The therapeutic gum irrigator of claim 6 further comprising a hinged door hingedly attached to said housing and covering said opening, said hinged door forming a liquid-tight seal with said housing.

8. The therapeutic gum irrigator of claim 6, in combination with a fill cup configured to receive the fluid, the fill cup having a pour spout sized to facilitate entry of the fluid through said opening.

9. The therapeutic gum irrigator of claim 1, wherein
   said pump includes a displacing element movable between a first position and a second position, and a biasing element biasing said displacing element to a first position;
   a user-operated lever is hingedly connected to said housing and configured to mechanically move said displacing element to a second position upon actuation by the user, thereby expelling a predefined volume of the fluid through said cannula, said biasing element causing said displacing element to return to said first position upon release of said user-operated lever by the user.

10. The therapeutic gum irrigator of claim 9, wherein said predefined volume is selected to be within a range of about 1-4 ml.

11. The therapeutic gum irrigator of claim 1, wherein the cannula is translucent or transparent.

* * * * *